(12) United States Patent
Kuhlman et al.

(10) Patent No.: US 7,098,454 B2
(45) Date of Patent: Aug. 29, 2006

(54) METHOD OF SAMPLE PREPARATION FOR ATOM PROBES AND SOURCE OF SPECIMENS

(75) Inventors: Kimberly Kuhlman, Shadow Hills, CA (US); James R. Wishard, Granada Hills, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/629,015

(22) Filed: Jul. 29, 2003

(65) Prior Publication Data

US 2004/0056195 A1 Mar. 25, 2004

Related U.S. Application Data

(60) Provisional application No. 60/401,428, filed on Aug. 5, 2002.

(51) Int. Cl.
*G01N 1/00* (2006.01)
(52) U.S. Cl. .......................................... 250/307; 250/306
(58) Field of Classification Search ................ 250/307, 250/304, 306, 309, 492.21; 216/2; 438/14
See application file for complete search history.

(56) References Cited

U.S. PATENT DOCUMENTS

| | | | |
|---|---|---|---|
| 5,193,595 A * | 3/1993 | Johnson et al. ........... | 144/136.1 |
| 5,501,893 A | 3/1996 | Laermer et al. | |
| 6,576,900 B1 * | 6/2003 | Kelly et al. ................ | 250/307 |
| 6,700,121 B1 | 3/2004 | Kelly et al. | |

FOREIGN PATENT DOCUMENTS

JP 3266995 1/2002

OTHER PUBLICATIONS

Preparation of 3D Atom Probe Samples of Multilayered Film Structures Using a Focused Ion Beam R. L. Martens, D. J. Larson, T. F. Kelly, A. Cerezo, P. H. Clifton and N. Tabat pp. 522-523—2000.

Focused ion-beam specimen preparation for atom probe field-ion microscopy characterization of multilayer film structures D. J. Larson, D. T. Foord, A. K. Petford-Long, A. Cerezo and G. D. W. Smith pp. 45-50, May 16, 1998.

Three-dimensional atom probe feldd-ion microscopy observation of Cu/Co multilayer film structures DJ. Larson, A. K. Petford-Long, A. Cerezoand G. D. W. Smith pp. 1125-1127, vol. 73, No. 8, Applied Physics Letters, Aug. 24, 1998.

(Continued)

*Primary Examiner*—Kiet T. Nguyen
(74) *Attorney, Agent, or Firm*—Daniel L. Dawes; Myers Dawes Andras & Sherman

(57) ABSTRACT

A specimen for atom probe analysis is prepared by providing a slab of material from which the specimen will be taken; defining a plurality of posts in the slab by in the slab; removing at least one post from the slab; and mounting the post. The post is shaped to a tip shape suitable for use in the atom probe, such as by focused ion beam milling the post to a tip shape. Grooves are cross cut into the slab. If needed, each groove is filled with a supporting material prior to cutting a parallel or intersecting groove thereto. The invention is also defined as a source of specimens for use in atom probe sampling comprising a slab of material from which the specimen will be taken, which has been defined into a plurality of posts and from which slab at least one post is removed from the slab and mounted.

26 Claims, 9 Drawing Sheets

OTHER PUBLICATIONS

Advances in Atom Probe Specimen Fabrication from Planar Multilayer Thin Film Structures D. J. Larson, B. D. Wissman, R. L. Martens, R. J. Viellieux, T. F. Kelly, T. T. Gribb, H. F. Erskine and N. Tabat, pp. 24-31, Sep. 18, 2000.

* cited by examiner

METHOD OF SAMPLE PREPARATION FOR ATOM PROBES AND SOURCE OF SPECIMENS

RELATED APPLICATIONS

The present application is related to U.S. Provisional Patent Application Ser. No. 60/401,428, filed on Aug. 5, 2002, which is incorporated herein by reference and to which priority is claimed pursuant to 35 USC 119. The present application is also a continuation application related to U.S. patent application Ser. No. 10/629,015, filed on Jul. 29, 2003, and issued as U.S. Pat. No. 20040056195 on Mar. 25, 2004, which is incorporated herein by reference and to which priority is claimed pursuant to 35 USC 120.

BACKGROUND OF THE INVENTION

1. Field of the Invention

The invention relates to the field of atom probe field ion microscopy and in particular for application to materials that can not be prepared for atom probe field ion microscopy using electropolishing.

2. Description of the Prior Art

The frontiers of geology and material science are constantly pushing the limits of detection of elemental distributions to ever finer scales. Atom probe field ion microscopy (APFIM) is a highly attractive technique in these fields despite the inherent difficulties in analyzing semiconducting and insulating materials. The local electrode atom probe (LEAP) shows potential for overcoming some of the difficulties in analyzing low conductivity samples. The National Aeronautics and Space Administration (NASA) is developing a prototype miniature local electrode atom probe (Mini-LEAP) at the Jet Propulsion Laboratory (JPL) for in-situ implementation in remote and extraterrestrial environments.

In conjunction with the development of the Mini-LEAP, a conventional APFIM study of several poorly conducting materials, has been initiated. Previous attempts to study rutile ($TiO_2$) and magnetite ($Fe_3O_4$) have shown how difficult samples of poorly conducting materials are to prepare for APFIM analysis.

Sharp APFIM specimens are generally produced using straightforward electropolishing methods. However, metallic multilayered samples and samples with specific geometries are much more difficult to prepare using electropolishing. The focused ion beam (FIB) was first used by Larsen et. al. in 1998 to trim multilayered metallic samples for APFIM using line milling at low angles to the axis of the specimen. Later, in 1999 an annular milling pattern centered on the axis of the specimen was used by Larsen to mill sharp, cylindrical specimens of these metallic multilayers.

Camus, Melmed and Banfield introduced the method of sharp shards (MSS) in 1991 for preparing samples that are not amenable to chemical etching. Sharp shards alone proved insufficient for successful APFM and the technique was abandoned. Kuhlman, et al. (2001) took advantage of the advances in FIB milling in combination with the MSS to produce successful APFIM specimens of poorly conducting magnetite ($Fe_3O_4$). The current work takes advantage of advances in microelectronics fabrication to more precisely shape and sharpen poorly conducting materials into APFIM specimens. These specimens require far less FIB milling, a time-intensive and expensive procedure.

The prior method is called the method of sharp shards because it involves crushing the material of interest and selecting microscopic sharp shards of the material for use as specimens. Each selected shard is oriented with its sharp tip facing away from the tip of a stainless-steel pin and is glued to the tip of the pin by use of silver epoxy. The MSS method is extended by use of a focused ion beam (FIB) to make the shard very thin (relative to its length) and to make its tip cylindrical and even sharper. The method of sharp shards is extremely time-consuming because the selection of shards must be performed with the help of a microscope, the shards must be positioned on the pins by use of micromanipulators, and the irregularity of size and shape necessitates days of FIB milling to sharpen each shard.

BRIEF SUMMARY OF THE INVENTION

The invention is a method of preparation of specimens of nonelectropolishable materials for analysis by atom probes which is a superior alternative to the prior methods. In comparison with the prior method, the present method involves less processing time. Also, whereas the prior method yields irregularly shaped and sized specimens, the present developmental method offers the potential to prepare specimens of regular shape and size.

The invention is a method for the preparation of a specimen for atom probe sampling comprising the steps of providing a slab of material from which the specimen will be taken; defining a plurality of posts in the slab; removing at least one post from the slab; and mounting the post.

The method further comprises the step or multiple steps of shaping the post to a tip shape suitable for use in the atom probe, such as by focus-ion-beam milling the post to a tip shape.

In the illustrated embodiment the step of defining a plurality of posts in the slab comprises cross cutting grooves into the slab, such as by cutting intersecting grooves with a saw. If needed, the method includes the step of filling each groove with a supporting material prior to cutting a parallel or intersecting groove thereto.

In general, the step of defining a plurality of posts in the slab comprises forming a plurality of regularly shaped posts in the slab by uniformly removing material around each post to isolate each post from each other post in the plurality of posts, such as removing the material by mechanical, electrical or chemical means. The illustrated embodiment removes the material with a dicing saw. Electrical means include electrostatic discharge machining, chemical means include electrolytic and acid etching, and laser means include laser ablation.

The step of removing at least one post from the slab comprises fracturing a single post from the slab or a section can be separated from the slab, which section includes more than one post connected to the section.

The invention can also be defined as a source of specimens for use in atom probe sampling comprising a slab of material from which the specimen will be taken, which has been defined into a plurality of posts and from which slab at least one post is removed from the slab and mounted. The post has been shaped to a tip suitable for use in the atom probe, such as by cross cutting grooves into the slab. The shaped post is focus-ion-beam milled to a tip shape.

The source includes material having a geological composition in which case the slab has a flattened polished surface into which the posts are defined. In this manner a plurality of uniformly shaped specimens are made available in a cost effective and efficient manner. However, this is not to say that the surface of the slab may be left in an irregular form and specimens have an irregular tip end surface and varied length may be produced.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Prior to describing the improvements of the invention, it is best first to understand the details of the prior method improved by the invention. In the prior art, field ion tips were fabricated from samples of metamorphic magnetite ($Fe^3O^4$) crystals extracted from a polymetamorphosed, granulite-facies marble with the use of a focused ion beam (FIB) milling system. This particular magnetite was chosen for several reasons. First, magnetite is a common mineral on Earth and Mars. Second, magnetite is one of the more conductive minerals, having a resistivity of $52 \times 10^{-4}$ Ω cm. Finally, this particular magnetite contains disk-shaped precipitates approximately 40 nm in diameter, 1–3 nm thick and about $10^4$ platelets/$\mu m^3$. Qualitative energy-dispersive X-ray spectroscopy (EDXS) has shown that manganese is concentrated in these precipitates and aluminum may also be present. However, quantitative analysis has been limited by the thickness of this second phase. The precipitates may also assist in maintaining the mechanical integrity of the samples, mitigating the fracture mechanisms that have made parallel analyses of single-crystal rutile unsuccessful. These considerations make this magnetite particularly attractive for investigating and demonstrating the capabilities of the APFIM for geological materials.

Note that images in the figures have been taken on one particular sample of magnetite, 031300E, or semiconducting materials to illustrate the process of reducing a macroscopic rock to a field ion specimen suitable for the APFIM analysis. However, it must be expressly understood that the invention is not limited to metamorphic magnetite, but is generally applicable with modifications within the scope of the invention to any kind of material and in particular to geological materials.

Figure 6:
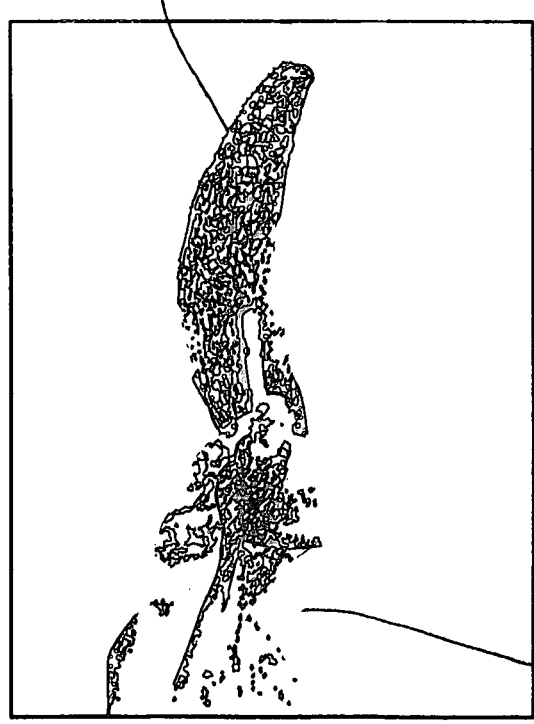
FIG. 6 is a focused ion beam electron image of magnetite sample taken from a shard according to the prior art with a Pt deposition at the base to improve electrical connection to the pin.

In the prior art the extracted metamorphic magnetite crystals averaged approximately 1–2 mm in diameter and were randomly crushed to make shards or samples 10 less than 200 μm in length. These shards 100 were placed on a glass microscope slide (not shown) and selected based on length and shape with a stereoscopic microscope. The tip of a stainless steel insect pin 102 mounted in a copper tube (not shown) was carefully loaded with a small amount of two-part, conductive silver epoxy 104. Micromanipulators were used to mount a suitably shaped fragment or sample 100 to the pin tip 102. The fragment 100 was then carefully straightened as depicted in the microphotograph of FIG. 6 with an electropolished wire probe (not shown) on a micromanipulator. Colinearity of the longitudinal shard axis and the longitudinal pin axis were found to be advantageous for successful analysis in the atom probe due in part to the limited range of motions of the specimen stage in an energy compensated position sensitive atom probe (ECOPoSAP). This colinearity also provides for the fabrication of a longer sample 100, facilitating resharpening of the tip 106 of shard 100.

Coatings have previously been deposited on nonconductive samples 100 for the APFIM analysis to improve the electrical properties of the samples 100. In the illustrated prior art method sample 10 was sputter-coated with about 50 nm of Cr after fabrication of tip 106. Analysis of the sample tips 106 after Cr deposition demonstrated a lack of control in achieving a uniform thin coating on a feature with a high aspect ratio. Although Pt is not generally the first choice of coating materials due to its low vapor pressure and high evaporation field, the ion-assisted deposition of Pt traces is easily accomplished in the FIB. Platinum traces were deposited on later samples 100 along the sides of the sample 100 and between the sample 100 and the stainless steel pin 102 in an attempt to improve the conductivity of the sample 100. The Pt traces were generally several micrometers in width, up to 100 μm in length and about 200 μm thick. Platinum was also deposited to fill in holes and craters created during the fabrication process. It is not clear if the Pt deposition improved the quality of the specimen because of the number of other variables involved in sample failure during atom probe analysis. However, it is thought that nonconductive samples 100 require coating to maintain conduction to the tip 106. These Pt traces might also improve the mechanical integrity of the samples 100 during analysis.

Figure 7:
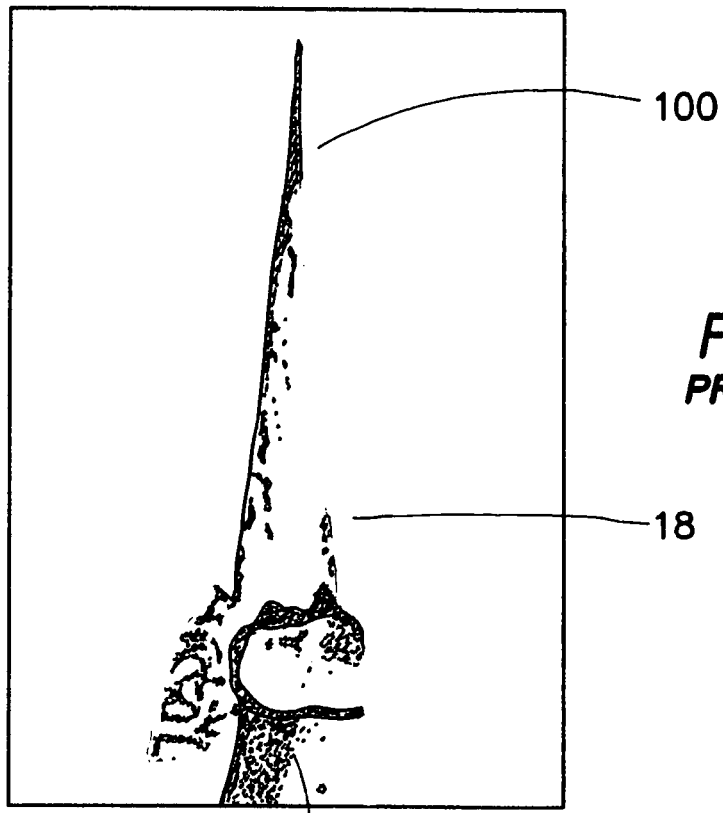
FIG. 7 is a transmission electron micrograph of the shard sample of FIG. 6 after extensive focus ion beam milling illustrating the smooth shank of the tip.

As can now be appreciated, in the prior art method the shaping of the sample 100 is a time-intensive effort. Once the epoxy had cured overnight, the samples 100 were loaded into an FEI 600 FIB capable of 25 keV Ga beam currents up to 4000 pA and equipped with an ion-assisted platinum deposition system. Sample 031300E prior to milling with the FIB is shown in FIG. 6. The sample 100 after the removal of a considerable amount of material is shown in FIG. 7. The shaping was accomplished by gross milling with high beam currents, followed by progressively finer milling with decreasing beam currents near the tip 106. Some samples 100 have shown evidence of melting due to high beam currents. This observation led to the adoption of smaller beam currents near the tip 106, increasing the sample preparation time.

Once the basic shape of the tip 106 had been achieved by a series of cuts, the sample 100 was tilted so that its major axis was parallel to the beam direction. An annular milling pattern was generated based on the diameter of the base of the sample 100 to reduce the amount of cratering around the circumference of the shank 108 of the sample 100 where it is attached to pin 102. Such cratering introduces potential points for mechanical failure. The initial annular milling was done with a relatively high beam current (about 1000 pA). The interior hole of the pattern, where no milling occurs, was made progressively smaller to carve out a round tip 106. The beam current was reduced to 16 pA for the final shaping cut. Some circumferential cratering was unavoidable and was minimized by tilting the sample 100 and removing extraneous protrusions while the sample 100 was in profile. FIG. 7 shows the sample 100 after final annular milling. Note that some of the Pt traces remain at the base of the magnetite after milling because the FIB allows for fine control of the beam size and location.

Figure 8:
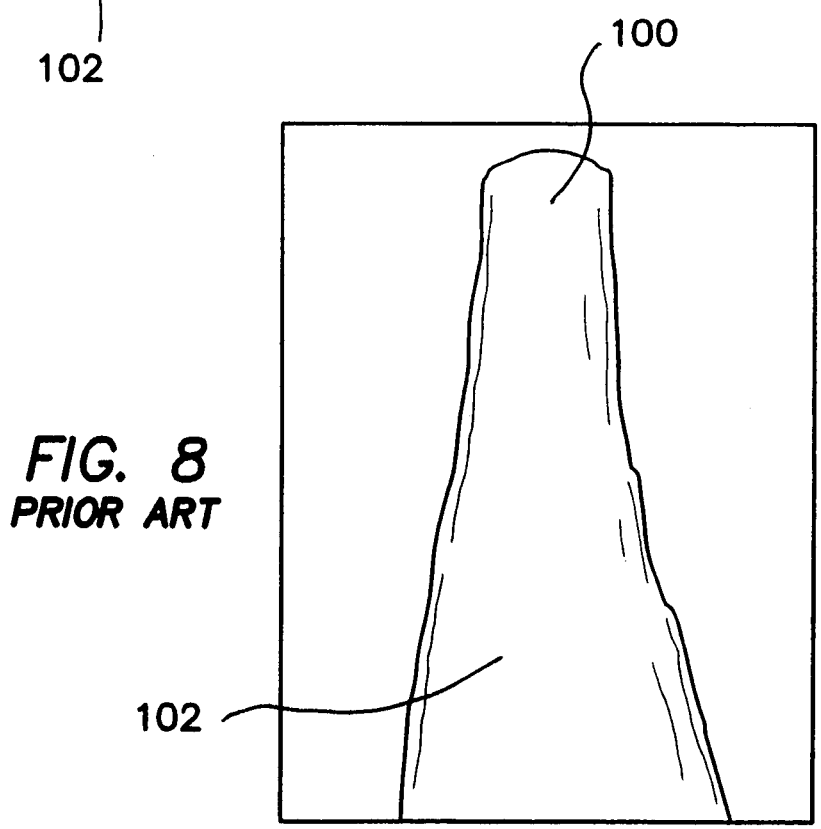
FIG. 8 is a transmission electron micrograph of the shard sample of FIG. 7 after analysis in the energy compensated position sensitive atom probe (ECOPoSAP) showing a slight roughness at the tip.

The prepared samples were examined in the Phillips CM30 transmission electron microscope (TEM) at ORNL operated at 300 keV. FIG. 7 shows sample 031300E after preparation with the FIB was completed. The radius of curvature of the tip 106 is approximately 25 nm. As the tip 106 was fabricated by sputtering the sample with 25 keV Ga⁺ ions, implantation of Ga is of great concern. An amorphous layer about 10 nm thick at the tip 106 and decreasing in thickness along the shank 108 was created during the FIB milling. However, the sample was sufficiently sharp that this damaged layer was field evaporated prior to the APFIM analysis. After ion milling in the FIB, a sample 100 with suitable geometry as shown in FIGS. 7 and 8, could be milled in a dual beam ion mill to resharpen the tip 106 if desired.

The careful and lengthy sample preparation techniques of the prior art method described above can be significantly reduced by using preformed diced posts 24 described below which are not only uniform, but initially machined to a shape and dimension closer to that ultimately needed in the atom probe tip. The basic finishing methodology described above is also practiced on the posts 24 of the invention, but with a great deal more ease, higher yield, fewer finishing steps and shorter finishing times.

Figure 1:
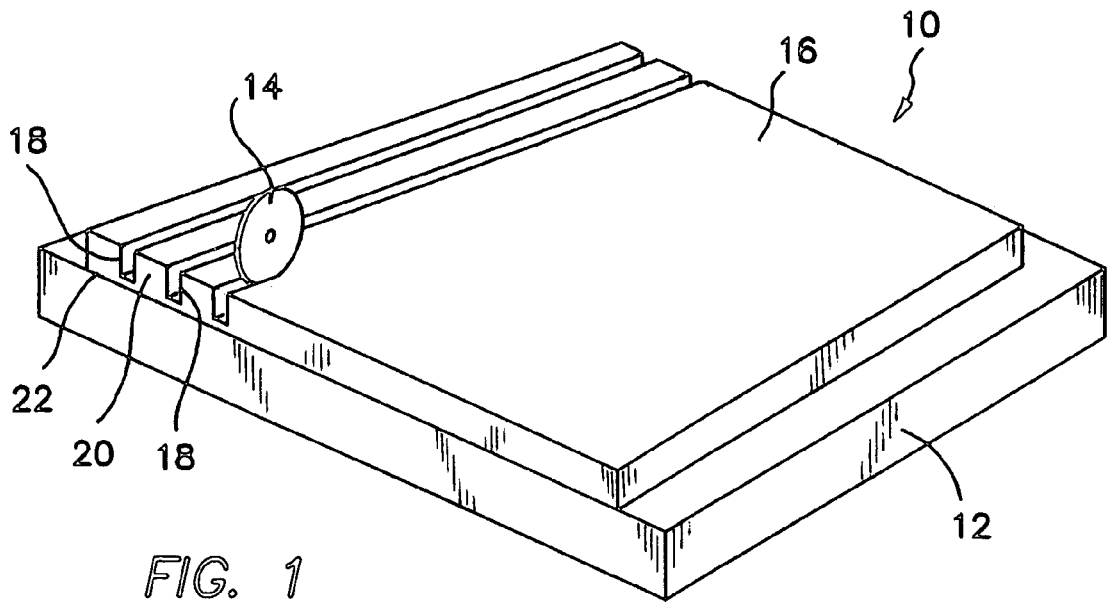
FIG. 1 is a simplified perspective diagram of a slab of material being cut by a saw with a plurality of parallel grooves to define a plurality of parallel ridges.
Figure 9:
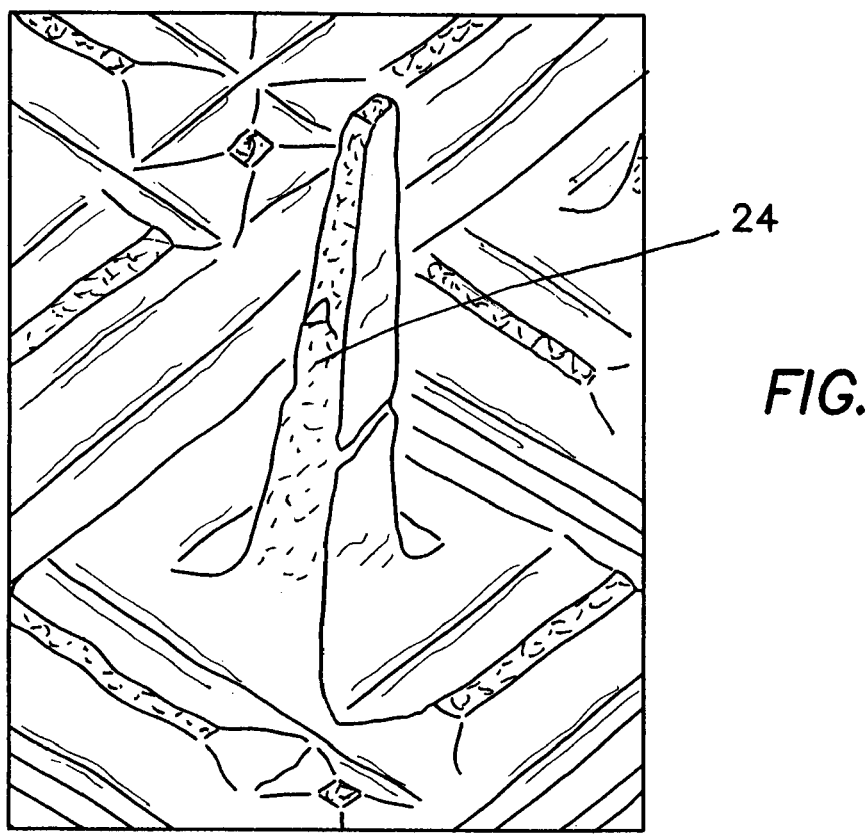
FIG. 9 is a scanning electron microphotograph of a single post sawn from a slab according to the invention.
Figure 10:
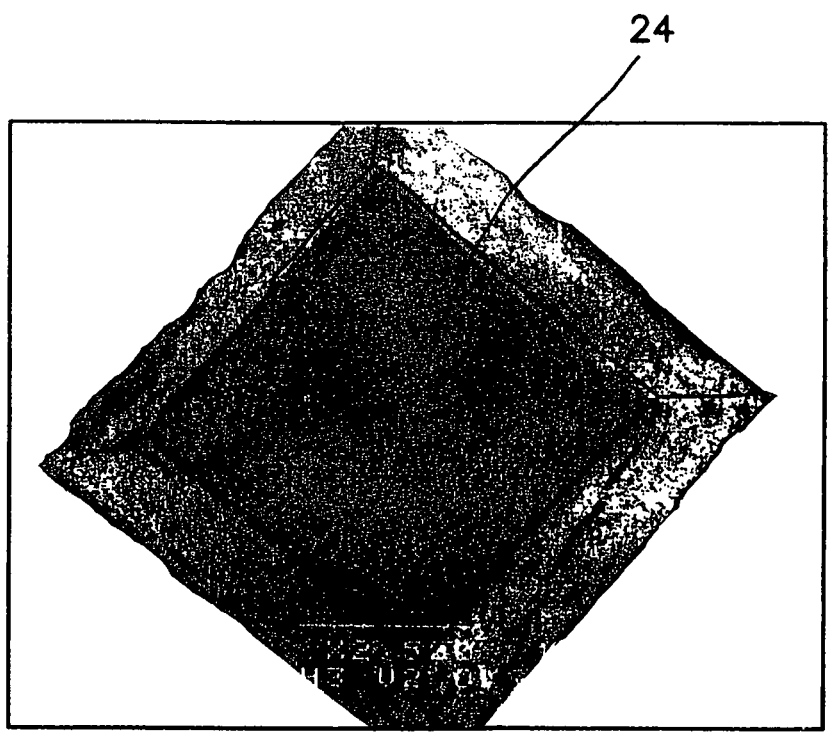
FIG. 10 is an enlarged scanning electron microphotograph of the end or tip of the single post of FIG. 9.

In the method of the invention, as diagrammatically shown in FIG. 1 a flat slab 10 of the material 16 of interest (e.g., a polished sample of rock or a coated semiconductor wafer) is mounted in the sample holder 12 (not shown) of a dicing saw of the type conventionally used to cut individual integrated circuits out of the wafers on which they are fabricated in batches. A saw blade 14 appropriate to the material 16 of interest is selected. The depth of cut 18 and the distance between successive parallel cuts 18 is made such that the lands 20 which are left after the cuts form a series of thin, parallel ridges on a solid base 22. For example, in FIG. 1 the depth of cut 18 is approximately 150–300 μm, with a width of cut 18 of 100 μm to several mm. It must be expressly understood that in addition to the diamond saw diagrammatically depicted in FIGS. 1 and 2 that any other means used for micromachining may be used such as electrostatic discharge machining, acid etching, saw cutting, and laser micromachining. A scanning electron microphotograph of a single post 24 sawn from magnetite is shown in FIG. 9 with an end view of post 24 in enlarged scale depicted in the scanning electron microphotograph of FIG. 10.

Figure 2:
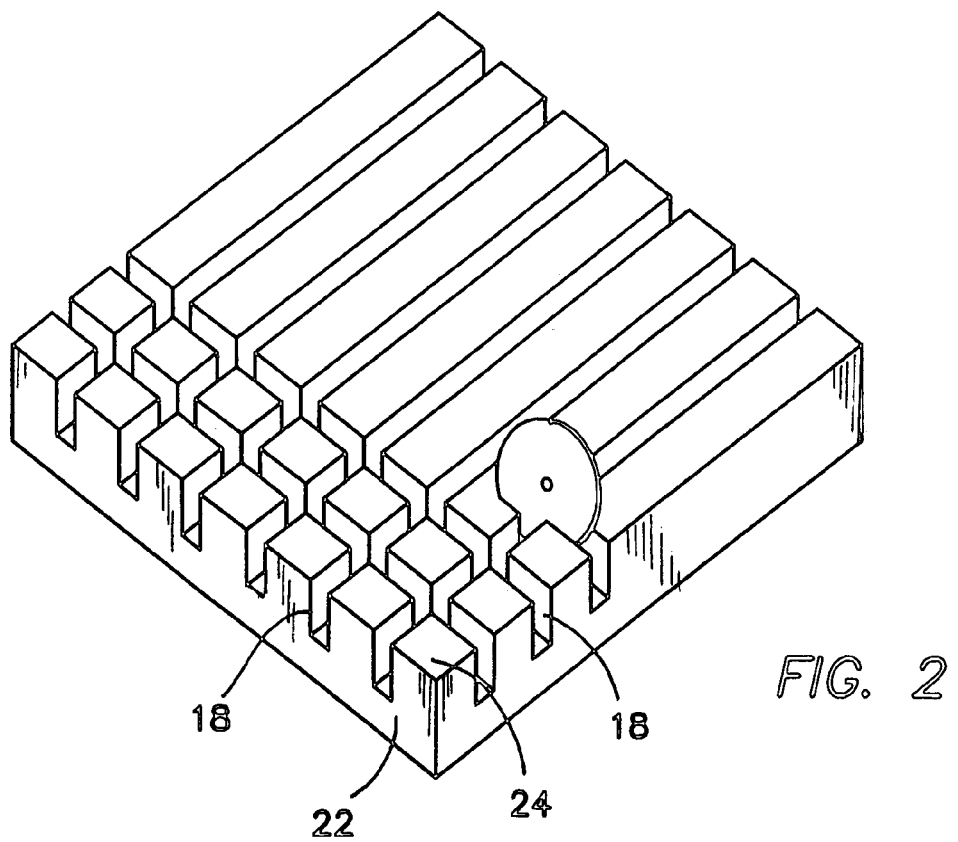
FIG. 2 is a simplified perspective diagram of a slab of the material of FIG. 1 being cut with a plurality of parallel grooves at right angles to the first set of grooves to define a plurality of posts.

Then the slab 10 is rotated and the pattern of cuts 18 is repeated, leaving behind a square array of square posts 24 5 to 20 μm on a side on the solid base 22 as shown in the diagrammatic depiction of FIG. 2. The posts 24 can be regular, long, and thin, as required for samples for atom probe analysis. For example in the above example, posts 24 are rectangular shapes typically 150–300 μm long and 5–20 μm square. Other shapes can be employed depending on the desired tip size to be fabricated from post 24 and the material brittleness. It is to be expressly understood that the shape of posts 24 is arbitrary as determined by the number and angulation of the cuts made. In the limit that a multiplicy of cuts are made, the posts progress through a multipolygonal cross section tending to a circular or elliptical cylinder.

Figure 3:
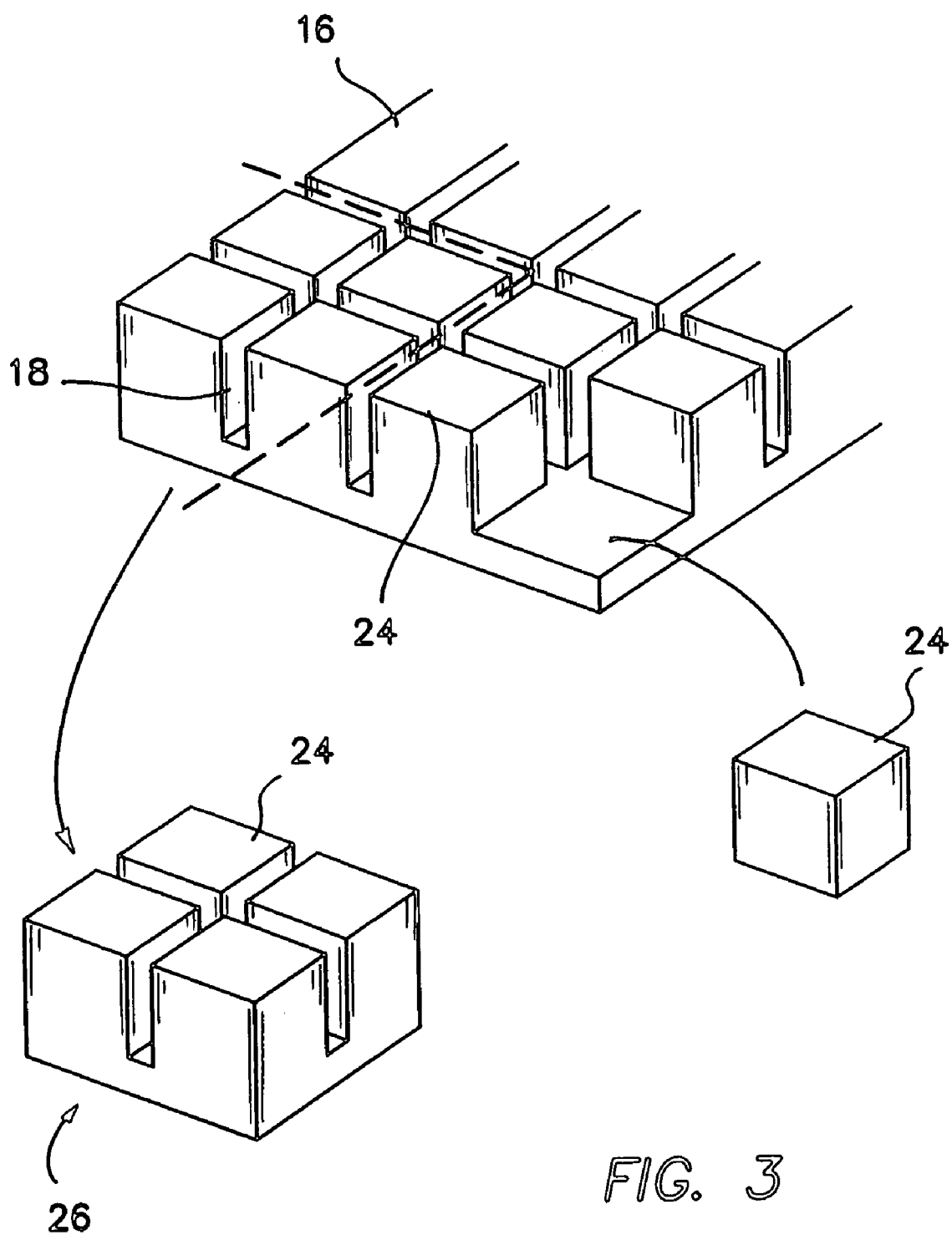
FIG. 3 is a simplified perspective diagram of a slab of material in which a single post is removed and in which a subplurality of posts have been removed as a unit.
Figure 4:
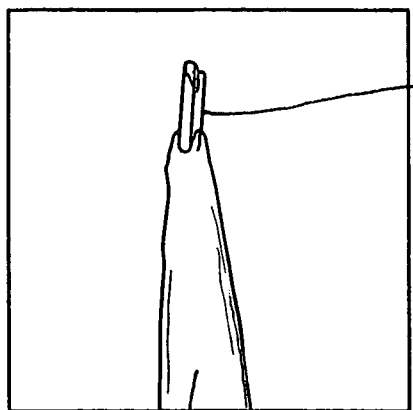
FIG. 4 is a perspective view of a microphotograph of a focus ion beam milled Si post of sawn from a slab as shown in FIG. 3 mounted on a pin on which post a grain of lunar regolith has been mounted.
Figure 5:
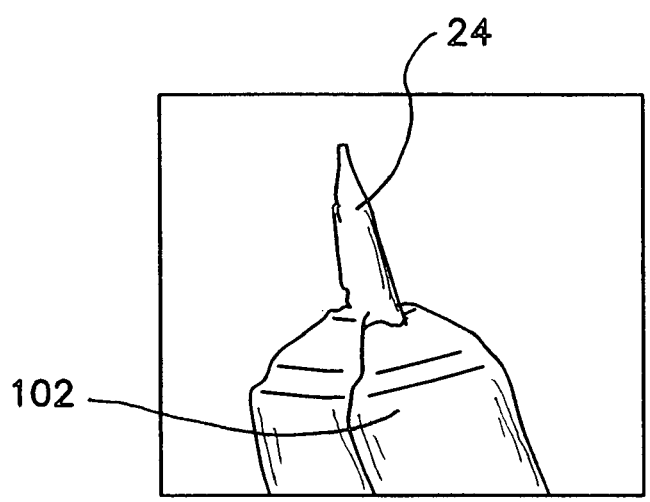
FIG. 5 is a micrograph of a diced or sawn sample after more extensive focused ion beam milling.
Figure 11:
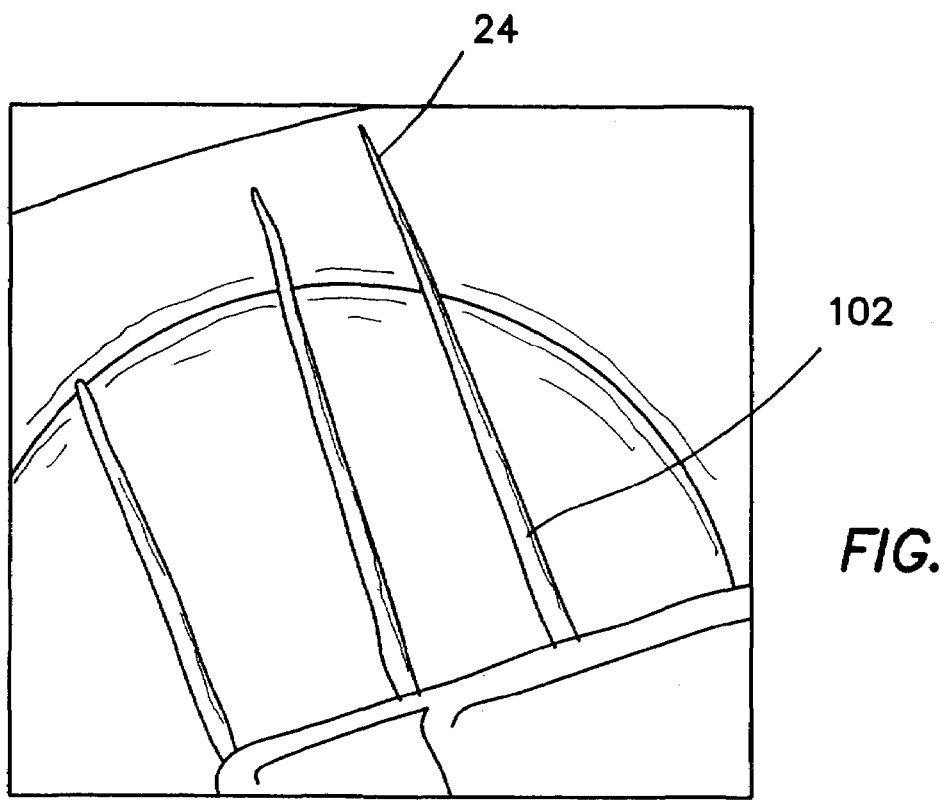
FIG. 11 is a side view enlargement of three pins, each with a diced post mounted on its tip.
Figure 12:
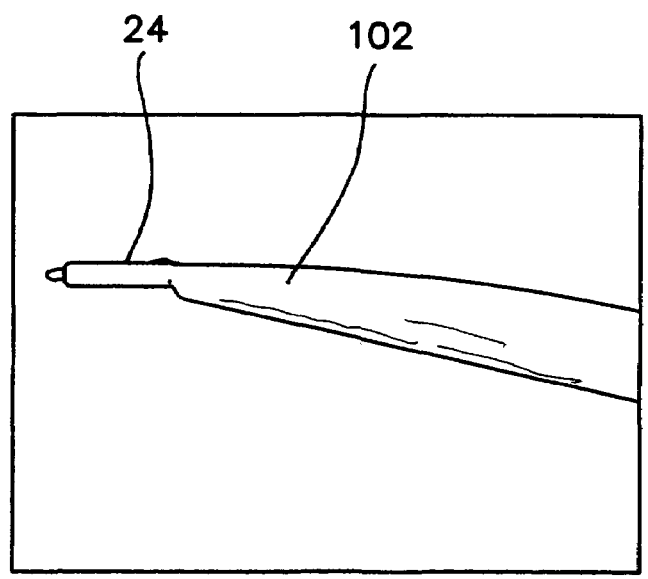
FIG. 12 is a side view enlargement of one of the pins of FIG. 11 with a diced Si post mounted on its tip a grain of lunar regolith mounted on the Si post.

Because of their regularity, the amount of FIB-milling time can be much less than that of the method of sharp shards 100 of the prior art. Individual posts 24 can be broken off as shown in FIG. 3 for mounting on pin 102 as shown in FIG. 4 in a manner similar to that of the method of sharp shards 100 and subsequent milling to a sharp tip 26 as depicted in FIG. 5. FIG. 11 is a microphotograph of a side view of three pins 102 onto which sawn posts 24 have been mounted. An enlarged microphotograph of a silicon post 24 on stainless steel pin 102 is shown in side view in FIG. 12. The post processing steps applied to post 24 are identical or similar to those applied to a shard as shown and described above in connection with FIGS. 5–9b. The post processing time is substantially reduced by the method of the invention. For example, whereas it would typically take approximately three days of work to prepare, mount and mill a single shard, the diced post 24 of the invention can be completely prepared, mounted and milled in about 4 hours.

Alternatively, the posts 24 can be left intact on the base 22 and the base 22 can be cut to a small square 26 (e.g., 3 by 3 mm) suitable for mounting in an atom probe of a design which is capable of accepting multiple-tip specimens. The advantage of multiple tip specimens is the possibility of analyzing many tips without the time consuming interchange of specimens. The cuts 18 in square 26 can be filled between the making of each cut 18 with a sacrificial supporting material, such as polymethylmethacrylate (PMMA), to provide structural support for lands 20 and/or posts 24 in the case that their brittleness or fragility prevents multiple cuts 18 from being made. The sacrificial supporting material remaining in cuts 18 can then be removed or chemically etched or dissolved once the last cut 18 has been made.

Figure 13:
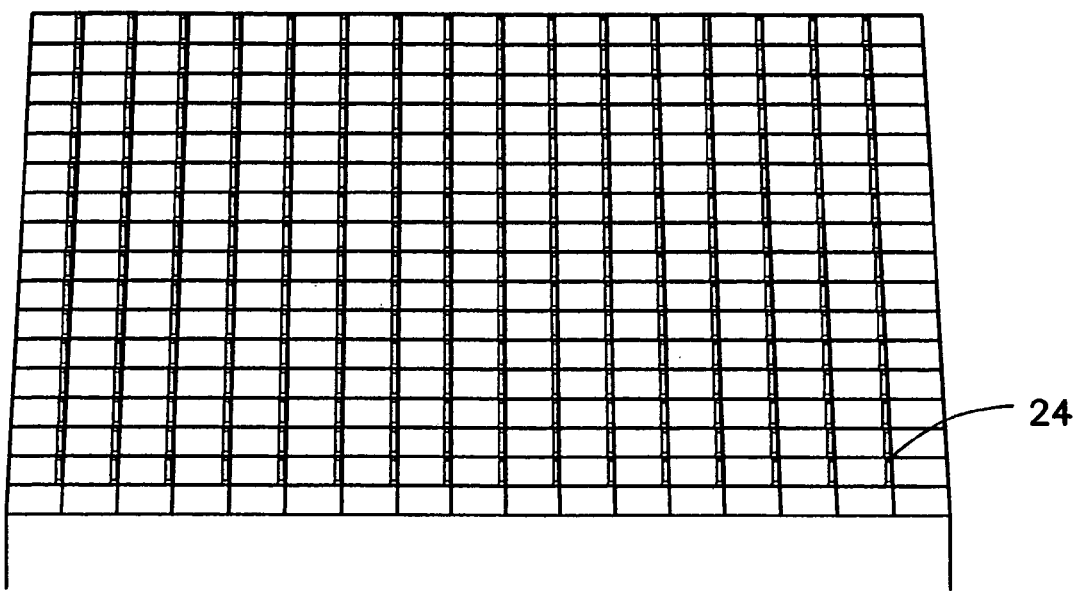
FIG. 13 is a perspective view of a microphotograph of an array of posts defined by dicing a semiconductor device.
Figure 14:
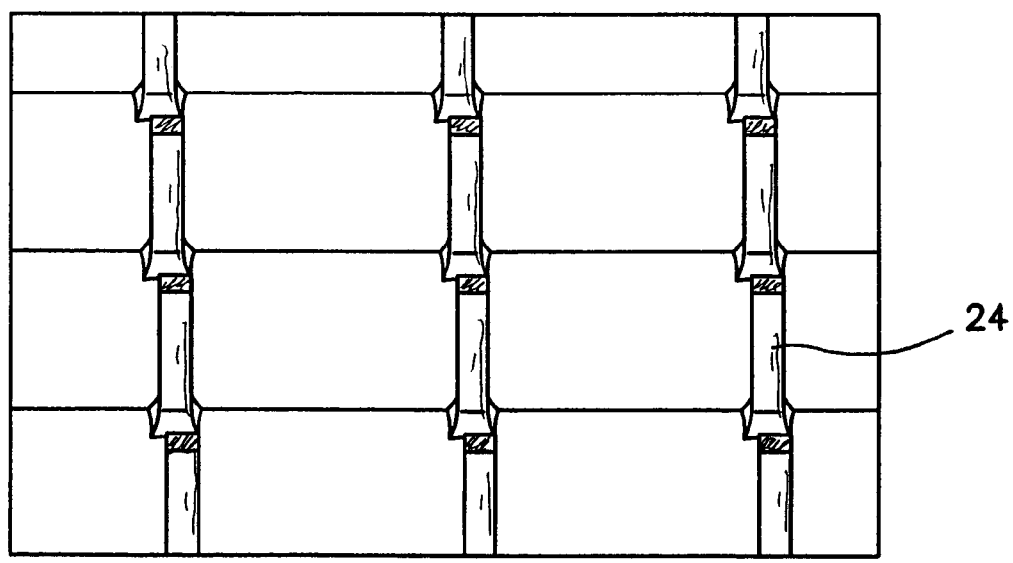
FIG. 14 is an enlargement of the perspective view of the microphotograph of the array of posts of FIG. 13.
Figure 15:
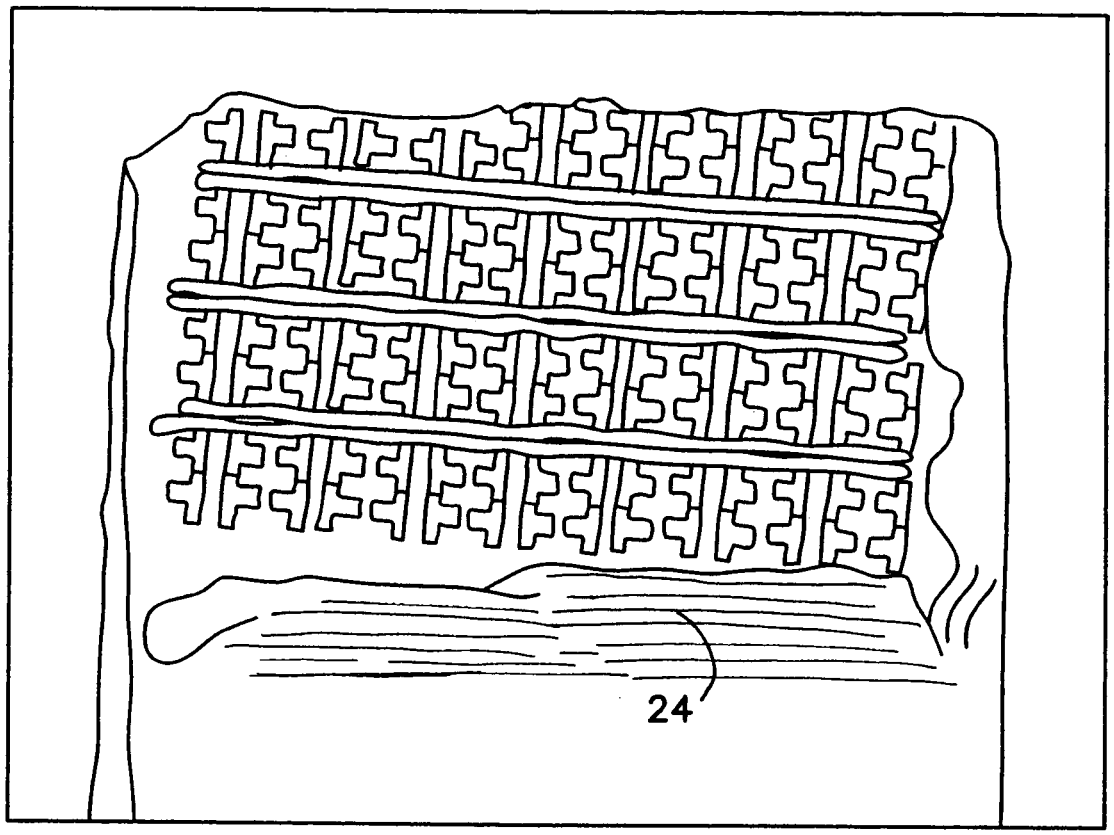
FIG. 15 is a perspective view of the end of one of the posts of the array of FIGS. 13 and 14 showing the structure of the semiconductor device.

FIG. 13 is an enlarged photograph of a perspective view of an array of square posts 24 cut into a semiconductor device. FIG. 14 is a microphotographic enlargement of the view of FIG. 13 showing a few of the posts 24 of the array. FIG. 15 is an enlarged microphotograph of the end or tip of a single post 24 of FIGS. 13 and 14 showing the printed circuit structure defined into the tip end. Post processing steps can be performed in an automated process on a ion beam mill on each of the posts 24 of the entire array of FIG. 13 without separately mounting each of the posts 24 on a corresponding pin 102 resulting in a considerable decrease in preparation time.

Furthermore by making the plurality of posts into a sparse array, sufficient distance is allowed between each of the posts 24 in the array such that each post can be used as an atom probe tip without interference from other posts 24 in the array and without disconnecting or removing it from the array and remounting it on a pin. Instead the array itself serves as the mounting stage and multiple samples in a single array can be tested or measured in an atom probe without time consuming repetitious multiple remountings or breaking vacuum in the atom probe.

Figure 16:
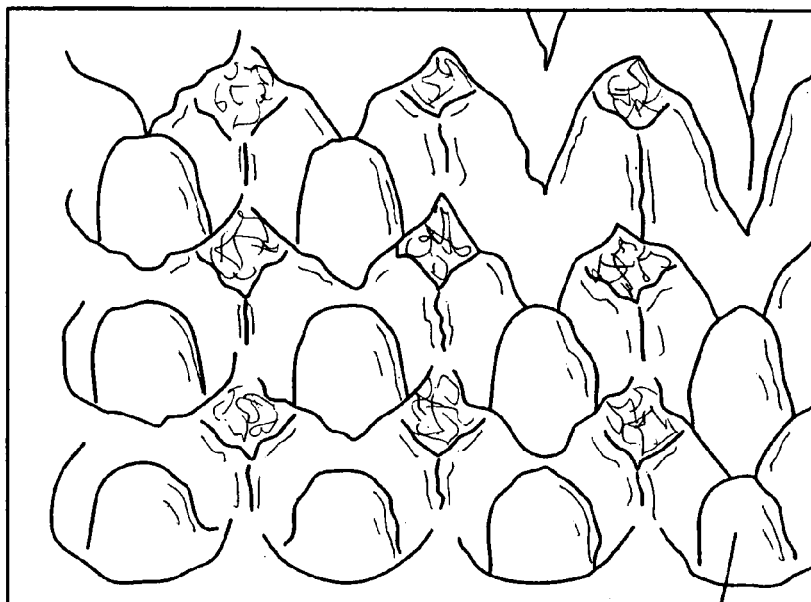
FIG. 16 is a perspective view of a microphotograph of an array of posts defined by laser ablation.
Figure 17:
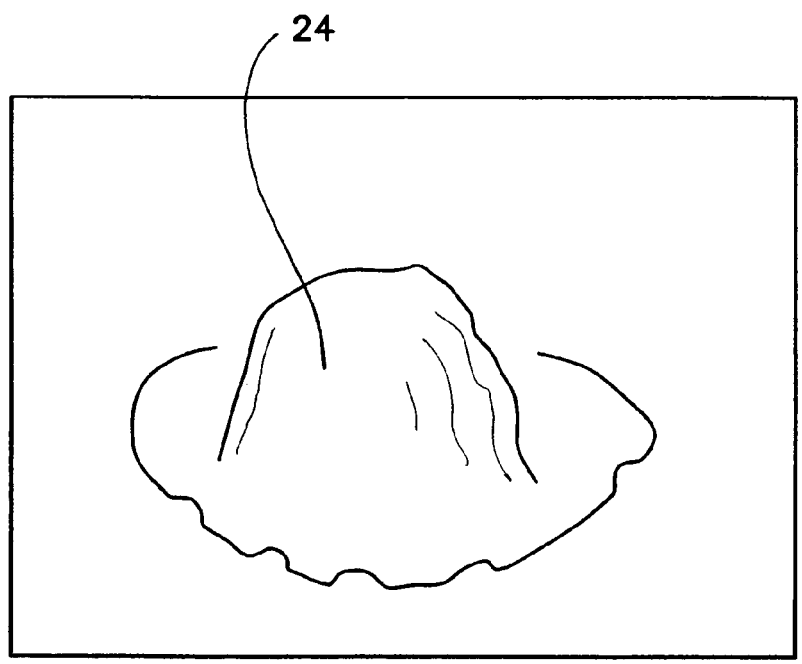
FIG. 17 is an enlarged perspective view of one of the posts of the array defined by laser ablation in FIG. 16.

While FIGS. 13–15 shown a sawn array, FIGS. 16 and 17 show a laser ablation array in which posts 24 have been defined as circular cylinders by laser ablation. Further ablation steps can be practices to remove the interlying material between posts 24, if desired.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for the preparation of a multiplicity of individual specimens for atom probe analysis comprising:
   providing a slab of material from which the specimen will be taken or analyzed;
   nonlithographically defining a plurality of removable high aspect ratio posts in the slab; and
   removing at least one post from the slab.

2. The method of claim 1 further comprising mounting the post on a pin.

3. The method of claim 2 where removing at least one post from the slab comprises fracturing a single post from the slab.

4. The method of claim 2 where removing at least one post from the slab comprises separating a section from the slab which section includes more than one post connected to the section to provide an array of posts.

5. The method of claim 1 further comprising shaping the post to a tip shape suitable for use in the atom probe.

6. The method of claim 5 where shaping the post to a tip shape suitable for use in the atom probe comprises focus-ion-beam milling the post to a tip shape.

7. The method of claim 1 where defining a plurality of posts in the slab comprises cross cutting grooves into the slab.

8. The method of claim 7 where cross cutting grooves into the slab comprising cutting intersecting grooves with a saw.

9. The method of claim 8 where cutting intersecting grooves with a saw comprises cutting at least two sets of parallel grooves at an arbitrarily chosen angle to each other.

10. The method of claim 1 where defining a plurality of posts in the slab comprises forming a plurality of regularly shaped posts in the slab by uniformly removing material around each post to isolate each post from each other post in the plurality of posts.

11. The method of claim 10 where uniformly removing material around each post to isolate each post from each other post in the plurality of posts comprises removing the material by mechanical means.

12. The method of claim 11 where removing the material by mechanical means comprises removing the material with a dicing saw.

13. The method of claim 10 where uniformly removing material around each post to isolate each post from each other post in the plurality of posts comprises removing the material by electrical means.

14. The method of claim 10 where uniformly removing material around each post to isolate each post from each other post in the plurality of posts comprises removing the material by chemical means.

15. The method of claim 1 further comprising shaping each of the posts to a tip shape suitable for use in the atom probe while each post remains connected to the section.

16. The method of claim 1 where defining a plurality of posts comprises shaping each of the posts so that the posts are spaced by a predetermined distance to avoid interference between separate posts when subsequently used in an atom probe.

17. A method for the preparation of a multiplicity of individual semiconductive or insulative specimens for atom probe analysis comprising:
providing a slab of semiconductive or insulative material from which the specimen will be taken or analyzed;
defining a plurality of regularly shaped high aspect ratio posts in the slab, the posts having a substantially quadrilateral cross section and a prismatic longitudinal axis, the posts being defined by grooves formed into the slab to the depth of the post as the starting material for the specimen; and
removing at least one post from the slab
where defining a plurality of posts in the slab comprises cross sawing grooves into the slab.

18. A method for the preparation of a multiplicity of individual nonmetallic specimens for atom probe analysis comprising:
providing a slab of material from which the specimen will be taken or analyzed;
nonlithographically defining a plurality of regularly shaped high aspect ratio posts in the slab to a depth of the post as the starting material for the specimen by uniformly removing material around each regularly shaped post to isolate each regularly shaped post from each other regularly shaped post in the plurality of regularly shaped posts;
removing at least one regularly shaped post from the slab; and
selectively removing additional material from the regularly shaped post.

19. The method of claim 18 where uniformly removing material around each post to isolate each post from each other post in the plurality of posts comprises removing the material by electrical means.

20. The method of claim 18 where removing the material around each post to isolate each post from each other post in the plurality of posts comprises removing the material with a dicing saw.

21. The method of claim 18 where removing at least one post from the slab comprises fracturing a plurality of posts from the slab to provide separate specimens.

22. The method of claim 18 where removing at least one post from the slab comprises separating a section from the slab which section includes a plurality of posts which remain connected to the section to provide an array of specimens.

23. The method of claim 22 further comprising shaping each of the posts of the array to a tip shape suitable for use in atom probe analysis while each post remains connected to the section.

24. The method of claim 23 where shaping each of posts comprises shaping each of the posts of the array so that the posts are spaced by a predetermined distance to avoid interference between separate posts when subsequently used in atom probe analysis.

25. A method for the mass produced preparation of individual specimens for atom probe analysis comprising:
providing a slab of material from which the specimen will be taken or analyzed;
defining a plurality of high aspect ratio posts in the slab by sawing intersecting microgrooves in the slab to the depth of the post to provide an array of posts, which is separable from the slab by mechanical fracturing;
removing at least one post from the array; and
machining the at least one post using a focused ion beam to produce the individual specimen.

26. A source for mass produced specimens for use in atom probe analysis comprising a slab of material from which the specimen will be taken into which material intersecting microgrooves have been sawed to a predetermined depth to define a plurality of high aspect ratio posts, which depth is determined by the separability of the posts from the slab by mechanical fracturing.

* * * * *